(12) United States Patent
Williamson (10) Patent No.: US 12,364,620 B1
(45) Date of Patent: Jul. 22, 2025

(54) ARM SUPPORTING AIR FLIGHT COMFORT SYSTEM

(71) Applicant: Wesley B. Williamson, Dunsbourgh (AU)

(72) Inventor: Wesley B. Williamson, Dunsbourgh (AU)

( * ) Notice: Subject to any disclaimer, the term of this patent is extended or adjusted under 35 U.S.C. 154(b) by 0 days.

(21) Appl. No.: 18/805,240

(22) Filed: Aug. 14, 2024

Related U.S. Application Data (60) Provisional application No. 63/524,710, filed on Aug. 14, 2023.

(51) Int. Cl.
*A61F 5/37* (2006.01)
*A47C 16/00* (2006.01)

(52) U.S. Cl.
CPC ............ *A61F 5/3738* (2013.01); *A47C 16/00* (2013.01); *A61F 5/373* (2013.01); *A61F 5/3761* (2013.01)

(58) Field of Classification Search
CPC ...... A61F 5/3738; A61F 5/373; A61F 5/3761; A47C 16/00
USPC .......................... 602/4, 28, 29; 2/69, 70, 72; 248/118–118.5
See application file for complete search history.

(56) References Cited

U.S. PATENT DOCUMENTS

| | | | | |
|---|---|---|---|---|
| 2,560,243 A * | 7/1951 | Peterson | ............... | A61F 5/3746 D24/190 |
| 2,796,862 A * | 6/1957 | Borntraeger | .......... | A61F 5/3738 602/4 |
| 3,371,663 A * | 3/1968 | Apgar | .................... | A61F 5/3738 602/4 |
| 7,954,187 B1 * | 6/2011 | Earnest | ................. | A61F 5/3723 5/482 |
| 10,499,696 B2 * | 12/2019 | Mitchell | ................ | A41D 23/00 |
| 11,135,465 B1 * | 10/2021 | Melendez | .......... | A63B 21/0442 |
| 2015/0296898 A1 * | 10/2015 | Bowen | ................... | A47K 10/02 2/69 |
| 2017/0036573 A1 * | 2/2017 | Webb | .................... | A47G 9/1063 |
| 2017/0208881 A1 * | 7/2017 | Leathers | ............... | A41D 23/00 |
| 2017/0231300 A1 * | 8/2017 | Leslie | .................... | A41D 15/04 602/4 |
| 2018/0020750 A1 * | 1/2018 | Nam | ...................... | D04B 15/36 2/69 |
| 2022/0265456 A1 * | 8/2022 | Osse | ..................... | A61F 5/3738 |
| 2023/0210681 A1 * | 7/2023 | Lance | ................... | A61F 5/3715 602/4 |

OTHER PUBLICATIONS

Armbie—over the head dual arm sling, Jan. 27, 2024.
Compression shirt—around arms and torso restriction garment, Apr. 1, 2024.

* cited by examiner

*Primary Examiner* — Muhammad Ijaz
(74) *Attorney, Agent, or Firm* — AVEK IP, LLC (57) ABSTRACT

A device for comfortably securing a user's arms while traveling, comprising one or more sheets of a fabric material which are formed into an article with a rounded pouch shape which comprises a top side, a bottom side, a left elbow pocket, and a right elbow pocket. The top of the device includes a hollow opening for inserting the user's arms into the article, which is sized to accommodate one or more dimensions of the user's arms while in a comfortable folded posture. The device secures the user's arms by providing a resistant compression force against the user's arms to prevent separation; maintaining the user's comfortable folded-arm posture.

20 Claims, 5 Drawing Sheets

ARM SUPPORTING AIR FLIGHT COMFORT SYSTEM

RELATED APPLICATIONS

This application claims priority to U.S. Provisional Application No. 63/524,710, filed on Aug. 14, 2023, the entire disclosure of which is incorporated herein by reference.

BACKGROUND OF THE INVENTION

Field of the Invention

The invention relates generally to the field of wearable user products, and more specifically, to a device for comfortably securing a user's arms during seated travel.

Description of Related Art

U.S. Pat. No. 7,300,410 "Webber" discloses an arm support in a sling with a pillow for supporting and restraining a user's arms.

U.S. Pat. No. 8,375,486 "Earnest" discloses a swaddling accessory for restraining a child's arms during sleep using hook and loop fastener connections.

U.S. 2017/0036573 "Webb" discloses a human arm support apparatus which requires the use of a large and rigid over-the-head vest-style device with a supporting pouch and/or arm slings. Webb's arm supports do not provide compression forces which hold the elbows at a set position, and instead the device provides vertical forces to lift the forearms while resting.

SUMMARY

In some aspects, the techniques described herein relate to a device for comfortably securing a user's arms while traveling, the device including: one or more sheets of a fabric material which are formed into an article with a rounded pouch shape, including a top side, a bottom side, a left elbow pocket, and a right elbow pocket; and a hollow opening, located on the top side of the article, for inserting the user's arms into the article; wherein the hollow opening is sized to accommodate one or more dimensions of the user's arms while in a comfortable folded posture; and wherein the article provides a resistant compression force against the user's arms to prevent separation and maintain the comfortable folded posture.

In some aspects, the techniques described herein relate to a device, wherein the hollow opening is sized according to a fixed set of dimensions selected according to a plurality of pre-set user sizes.

In some aspects, the techniques described herein relate to a device, further including an adjusting element configured to increase or reduce one or more dimensions of the hollow opening.

In some aspects, the techniques described herein relate to an adjusting element, wherein the adjusting element includes a fixing point located on an inner surface of the article which is fastened to an adjustable upper edge located on an inner fold loop of the article.

In some aspects, the techniques described herein relate to an adjusting element, wherein the fixing point and the adjustable upper edge are connected via a hook and loop fastener.

In some aspects, the techniques described herein relate to a device, wherein the left elbow pocket and the right elbow pocket are separated fabric elements, and wherein the left and right elbow pockets are connected to one another, at one or more of their ends, by one or more of the following: an elastic band; or an adjustable strap.

In some aspects, the techniques described herein relate to a device, wherein the article further includes: an elastic band reinforcing and providing compression force on a top edge of the article's hollow opening.

In some aspects, the techniques described herein relate to a device, wherein an outer surface of the article further includes one or more decorative elements, printed images, or other aesthetic modifications.

In some aspects, the techniques described herein relate to a device, wherein the article further includes an interior lining material which is comfortable for extended contact with human skin.

In some aspects, the techniques described herein relate to a system for comfortably securing a user's body during extended travel, the system including: at least one device for securing a user's body position, the device including: one or more sheets of a fabric material which are formed into an article with a rounded pouch shape, including a top side, a bottom side, a left elbow pocket, and a right elbow pocket; and a hollow opening, located on the top side of the article, for inserting the user's arms into the article; wherein the hollow opening is sized to accommodate one or more dimensions of the user's arms while in a comfortable folded posture; wherein the article provides a resistant compression force against the user's arms, such that the user's arms are prevented from separating and remain in the comfortable folded posture; and wherein the article is configured to be highly flexible, such that the device can perform one or more secondary functions, including: securing the article to a fixed element within a travel environment, such that a preferred upper-body posture of the user can be supported by the secured article; providing a compression force which prevents the user's knees from spreading beyond a set distance; or providing a suspended footrest, by securing a bottom of the user's feet to an object within a travel environment.

In some aspects, the techniques described herein relate to a system, wherein the one or more secondary functions further include configurations for performing exercise maneuvers, using the at least one device as a resistive elastic exercise band.

In some aspects, the techniques described herein relate to a system, wherein the hollow opening of the at least one device is sized according to a fixed set of dimensions selected according to a plurality of pre-set user sizes.

In some aspects, the techniques described herein relate to a system, wherein the at least one device further includes an adjusting element configured to increase or reduce one or more dimensions of the hollow opening.

In some aspects, the techniques described herein relate to an adjusting element, wherein the adjusting element includes a fixing point located on an inner surface of the article which is fastened to an adjustable upper edge located on an inner fold loop of the article.

In some aspects, the techniques described herein relate to an adjusting element, wherein the fixing point and the adjustable upper edge are connected via a hook and loop fastener.

In some aspects, the techniques described herein relate to a system, wherein the left elbow pocket and the right elbow pocket of the at least one device are separated fabric elements, and wherein the left and right elbow pockets are connected to one another, at one or more of their ends, by one or more of the following: an elastic band; or an adjustable strap.

In some aspects, the techniques described herein relate to a system, wherein the at least one device further includes an elastic band reinforcing and providing compression force on a top edge of the article's hollow opening.

In some aspects, the techniques described herein relate to a system, wherein an outer surface of the article of the at least one device further includes one or more decorative elements, printed images, or other aesthetic modifications.

In some aspects, the techniques described herein relate to a system, wherein the at least one device further includes a lining material on the interior of the article which is comfortable for extended contact with human skin.

In some aspects, the techniques described herein relate to a system for comfortably securing a user's body during travel on an airplane, the system including: a plurality of devices, wherein the devices include: one or more sheets of a fabric material which are formed into an article with a rounded pouch shape, including a top side, a bottom side, a left elbow pocket, and a right elbow pocket; and a hollow opening, located on the top side of the article, for inserting the user's arms into the article; wherein the hollow opening is sized to accommodate one or more dimensions of the user's arms while in a comfortable folded posture; wherein the article functionally replaces a traditional armrest, by providing a resistant compression force against the user's arms, such that the user's arms are prevented from separating and remain in the comfortable folded posture; wherein the article is configured to be highly flexible, such that the device can perform one or more secondary functions, including: securing the article to a headrest of a seat within a travel environment, such that a preferred upper-body posture of the user can be supported by the secured article; providing a compression force which prevents the user's knees from spreading beyond a set distance; or providing a suspended footrest, by securing a bottom of the user's feet to a tray table located in the travel environment; and wherein the plurality of devices are implemented by the user to perform a plurality of functions.

DETAILED DESCRIPTION

U.S. airlines carry almost one billion passengers every year, with a majority of these flights being at least several hours in duration. Due to size and fuel efficiency limitations, airlines offer very limited space and require passengers to sit in close proximity to at least one other person with a shared armrest. Since passengers seated together are often strangers, socially and physically uncomfortable situations can arise when one passenger inadvertently crosses into the seating area of another passenger, or when two passengers are contesting for the one shared armrest. Flying in a standard airline seat is already an uncomfortable and cramped experience, but this is made worse if an arm rest is not available and if passengers are accidentally bumping neighbors with their elbows and/or knees.

Current products to alleviate airline discomfort primarily focus on securing the head and neck. Individuals sleeping on airplanes are most often concerned with neck pain from poor neck posture, however, these products do little to maintain a good arm position or upper-body posture while sleeping. Often, passengers desire one or more armrests to brace their body against while sleeping to prevent slouching and back pain, again, leading to competition over the shared armrests. Likewise, passengers are at the greatest risk of unintentionally crossing into their neighbor's seating area while trying to sleep or relax, as they gradually lose awareness of their arm and upper-body positions. These issues lead to many uncomfortable and problematic encounters during flights, and beyond heavy and cumbersome weighted blankets/pillows, there are very few consumer products which can adequately address these issues. Accordingly, there exists a need in the art for a simple and highly-portable product which can comfortably secure the arms and/or upper body in a preferred posture, while eliminating a passengers need for a shared armrest.

As a solution to the problems detailed above, a device for comfortably securing a user's arms during travel is described. In the following detailed description, reference is made to specific example embodiments in by means of written descriptions and references to illustrations. These examples are described in sufficient detail to enable those skilled in the art to practice what is described and serve to illustrate how elements of these examples may be applied to various purposes or embodiments. Additional embodiments of the invention exist which would incorporate any functional, structural, or aesthetic modifications that may be made based on what is disclosed. Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combination is explicitly contemplated to be within the scope of the examples presented here. The following detailed description does not, therefore, limit the scope of what is claimed.

Particularly, an example embodiment of the invention is described in detail and illustrated in the drawings, wherein the arms-securing device is an article crafted from a single elongated strip of fabric which uses an inner fold with hook and loop fastener connection means to adjust the size of the device's arm opening. This described embodiment in no way limits the device to the shape or materials of the article shown, nor does it limit to means of adjusting the arm opening of the device to hook and loop fastener connections. The device claimed can encompass a plurality of additional article shapes and fastener connection means without diverging from the scope of what is claimed and disclosed in this detailed description.

Figure 1:
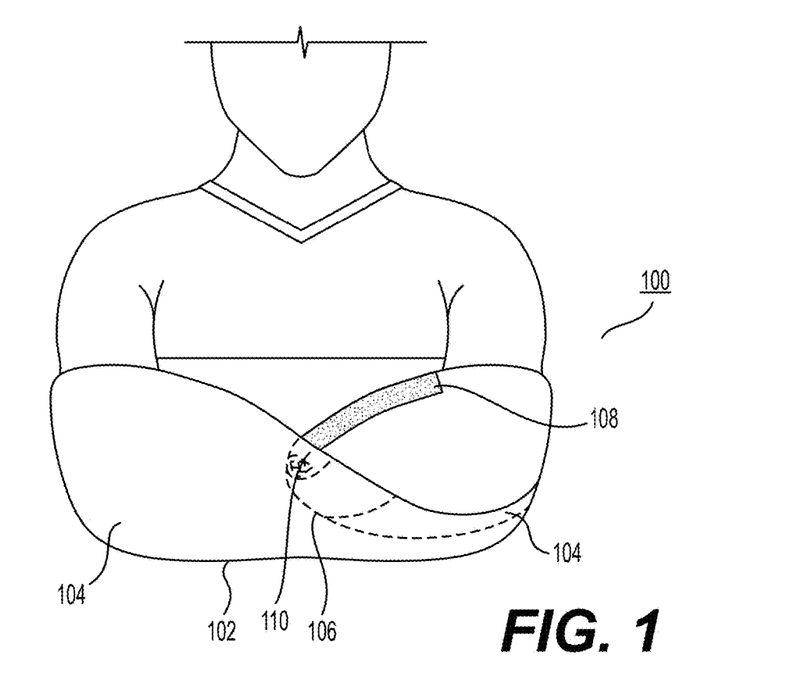
FIG. 1 shows a frontal view of the arm-securing device of the present invention.

First looking to FIG. 1, a front view of a preferred embodiment of the arms-securing device 100 is shown. The device 100 is comprised of an article 102 which is made of one or more sheets of a flexible material. In some embodiments this flexible material is a fabric or cloth made of natural, synthetic, or blended fibers, while in additional embodiments, the fabric may be a flexible strip of elastic, or any other type of flexible material suited for comfortably securing a user's arms. The article 102 is formed into a rounded pouch shape with a top and bottom. On the top of the article 102 is an opening for inserting the user's arms. The article is shaped to include elbow pockets 104 for the user's left and right elbows, and these pockets provide a natural point for the article 102 to gently compress the user's left and right elbows together to maintain a comfortable crossed-arms posture.

The opening of the article 102 can vary in size depending on one or more dimensions of the user's arms. In the preferred embodiment shown, this opening is adjustable by the user, such that the user can select an appropriate opening size of the article 102. One initial adjustment of the opening's size is typically necessary for the article to fit an individual appropriately, however, further adjustments by the user can be made to change the feel of the device 100. If the opening of the article 102 is made smaller, pressure caused by the device stretching over the user's arms will enact a greater compression force pressing the user's elbows together. Likewise, if the opening of the article 102 expanded, the compression forces acting on the user's elbows will be reduced for a looser fit. This allows the user to not only size the device 100 appropriately for their body shape, but also allows the user to change the feel and comfort of the device 100.

Figure 3:
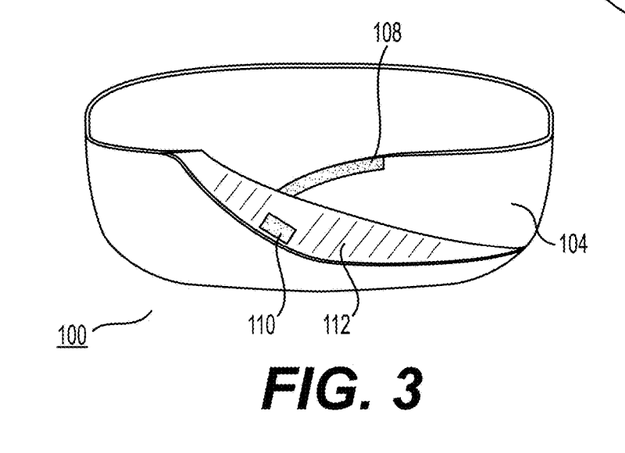
FIG. 3 shows a frontal view of the arms-securing device, with a front edge of the device's article folded downward to show the inner surface of the article and an adjusting element.

To change the opening size of the article 102, an adjusting element is included. One end of the article 102 is formed into an inner fold 106 which is pulled inside the article 102, such that by pulling the inner fold 106 further inside the article 102, the circumference of the overall article 102 is reduced and the opening is made smaller. The degree by which the article 102 may be adjusted is limited by the length of an adjustable upper edge 108. The adjustable inner edge 108 is a length of a hook and loop fastening material which is secured to the inner fold 106. Likewise, a fixing point 110 comprising a segment of a hook and loop fastening material compatible with the material of the adjustable inner edge 108, is secured to the inner wall of the article 112 (shown in FIG. 3) along the path of the adjustable inner edge 108. To maintain a selected size of the article 102, the fixing point 110 on the inner surface of the article 112 is secured to a selected location on the adjustable inner edge 108, fastening the inner fold 106 to the article 102 and preventing further movement.

The article 102 may be further modified to include one or more decorative elements (not shown) which improve the aesthetics of the device 100. For example, the article may include mass-printing or print-on-demand techniques to create unique and aesthetically pleasing images on the surface of the article 102. In further examples, the article 102 may have protruding design elements and textured patterns for improved visuals or for improving the tactile feel of the article 102 during handling. In yet further examples, the article may include cutout patterns and/or variations in shape which improve the aesthetics of the device, improve airflow to the user's arms, or provide other functional improvements known in the field of wearable devices.

Figure 2:
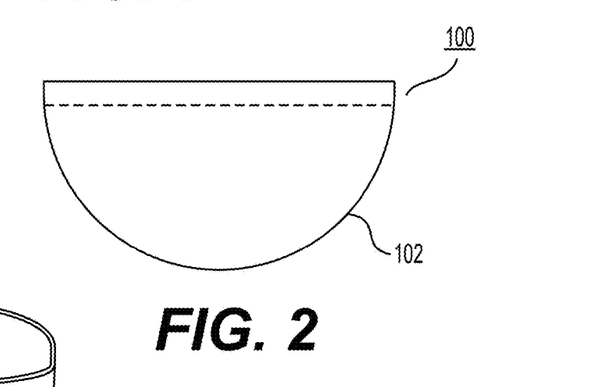
FIG. 2 shows a rear view of the arms-securing device.

The embodiment shown in FIG. 1 is a front-fastening configuration, wherein only the front of the article 102 comprises an adjusting element. The back of the article 102, as shown in FIG. 2, lacks any adjusting elements. Looking to FIG. 3, the fixing point 110 is shown on the inner surface of the article 112. In some embodiments, the article 102 is formed from only one material and the inner surface of the article 112 is the same material as the article 102. In an optional embodiment, the inner surface of the article 112 may be a separate material from the material of the article 102. The inner surface 112 material can be sewn to the inner lining of the article 102 and can be a material which is particularly suited for contact with human skin. This optional configuration allows the outer surface material of the article 102 to be a tougher material resistant to wear and damage, while the material of the inner surface 112 can be soft and comfortable for extended wear by the user.

Figure 4A:
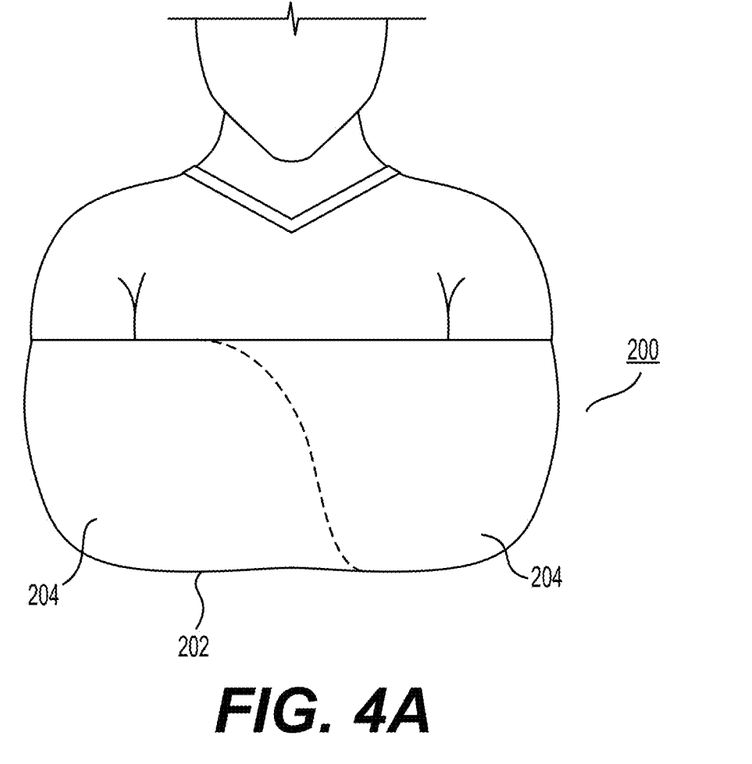
FIG. 4A shows a frontal view of an alternate embodiment of the invention, a rear-fastening version of the arms-securing device.
Figure 4B:
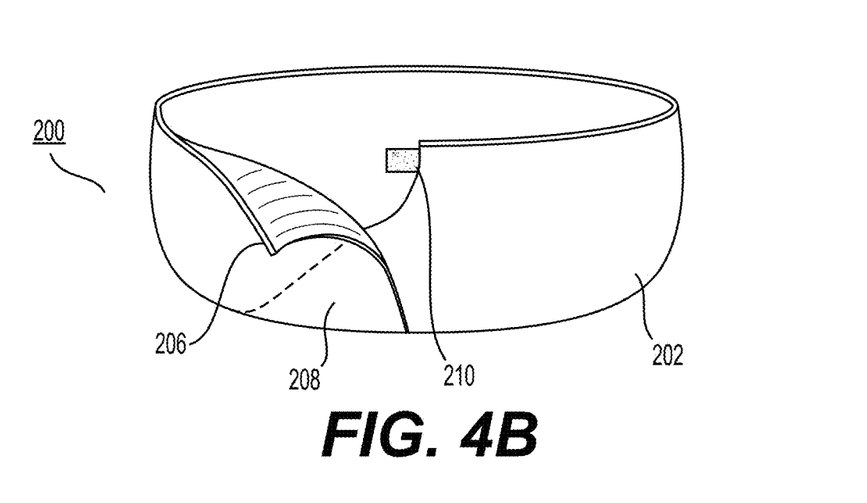
FIG. 4B shows a rear view of the alternate embodiment shown in FIG. 4A.

FIGS. 4A and 4B show an alternative embodiment of the invention, wherein, the front-fastening device 100 is instead a rear-fastening device 200 with an article 202 that has elbow pockets 204. FIG. 4A shows a front view of the device 200, in which the front of the article 202 does not include any adjusting elements. FIG. 4B shows the back side of the article 202, wherein an adjustable flap 206 is pulled over an inner fold 208 and secured in position by a fixing point 210. In some embodiments, the fixing point 210 uses hook and loop fasteners in the same fashion as the device 100 of FIG. 1. In additional embodiments, both the fixing point 210 of device 200 and the fixing point 110 of device 100 can be substituted with other fastening means.

Additional means for fastening can include buttons, snaps, draw strings, straps, and any other fastener means known in the art which can secure various types of articles. In an alternative embodiment, the various articles do not utilize an adjusting element or fastening means and are instead pre-sized to a set of known dimensions corresponding to a series of selectable size ranges; such as small, medium, large, etc. In yet further alternative embodiments, the various articles may be composed of a highly flexible material, such that a single device may stretch to accommodate a plurality of different user sizes.

Figure 5:
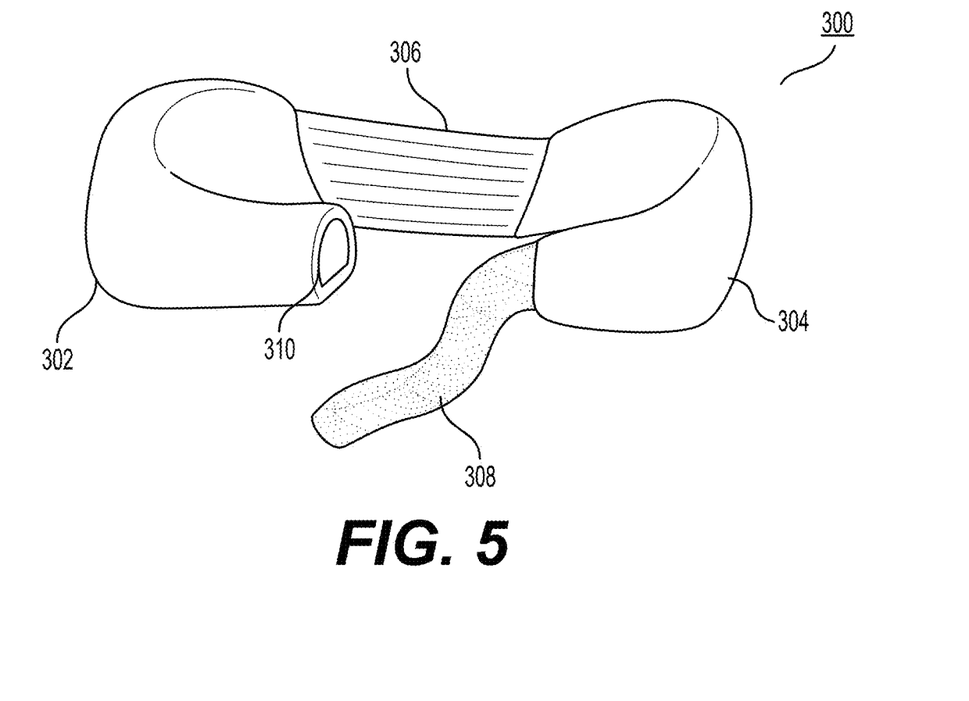
FIG. 5 shows a frontal view of an alternate embodiment of the invention, a two-article arms-securing device where the articles are connected by elastic bands and adjustable straps.

Next looking to FIG. 5, another alternative embodiment of the invention is shown, wherein, a device 300 comprises two separate articles 302, 304 which are secured to one another by a flexible band 306 and an adjustable strap 308. The user of device 300 places their elbows in articles 302, 304 and then threads the adjustable strap 308 through a connection point 310 to tighten the articles 302, 304 and comfortably secure their arms. This alternative embodiment offers additional advantages by increasing the user's ability to customize the size of the device 300, and better accommodate users with smaller and larger than normal body sizes. In some embodiments, the flexible band 306 may be a traditional elastic band, while in further embodiments, the flexible band 306 may be any band which provides a desired level of elasticity and compression force. In some embodiments, the adjustable strap 308 may be a traditional nylon strap, while in further embodiments, the adjustable strap may be any form of strap, string, or other connecting element known in the art. In the preferred embodiment shown in FIG. 5, only one flexible band 306 and one adjustable strap 308 are shown, however, in additional embodiments, flexible bands 306 and/or adjustable straps 308 may be added, removed, and/or substituted to achieve the same function.

Figure 6:
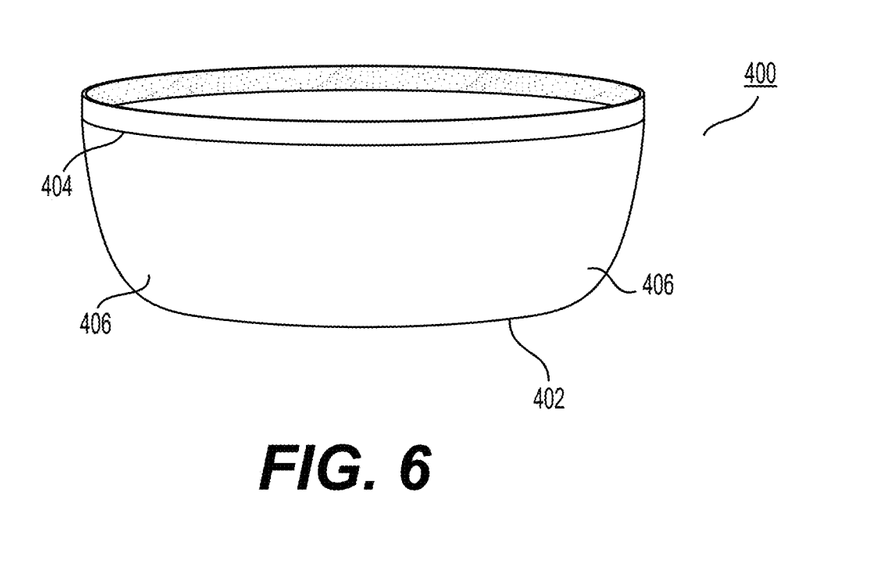
FIG. 6 shows a frontal view of an alternate embodiment of the invention, a single article arms-securing device with no adjustable elements and an elastic band located along the top edge of the article.

FIG. 6 shows another alternative embodiment of the invention, wherein, the device 400 comprises a pre-sized article 402 which does not have an adjusting elements. Device 400 further comprises a reinforcing elastic band 404 along the top edge of the article 402 in order to compress and secure the user's elbows placed in elbow pockets 406. This reinforcing elastic band 404 can be configured at various compression strengths according to a user's preferences and can even be implemented as a means of exercising the user's arms. The user may perform stretches with their arms/elbows while the band 404 provides resistive force, allowing the device 400 to function as both a relaxing arms-securing device for travel and as a piece of exercise equipment.

In alternative embodiments, the reinforcing elastic band 404 can be implemented on any of the devices 100, 200, 300, or any other additional embodiments of the invention, to achieve similar outcomes. In other optional embodiments, the reinforcing elastic band 404 may be located on other portions of the article 402, such as at the bottom by the elbow pockets 406 and may otherwise be implemented in numerous other functions and/or configurations of the various embodiments.

Figure 7A:
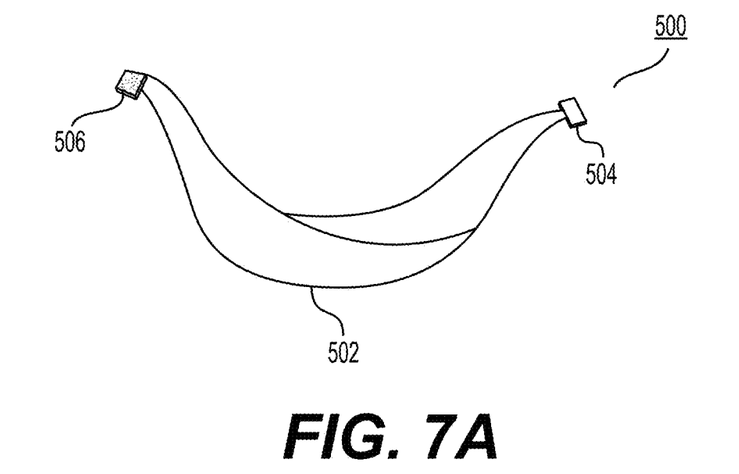
FIG. 7A shows a frontal view of an alternate embodiment of the invention, an arms-securing device with a hammock shaped article.

FIG. 7A shows yet another alternative embodiment of the invention, wherein the device 500 comprises an article 502 that is shaped like a hammock with a first securing element 504 and a second securing element 506 located on each respective end of the article 502. In a preferred embodiment, the article 502 is highly flexible and elastic, such that the device can stretch up to several feet in length. While the device 500 can be front or rear fastened by the securing elements 504, 506 to secure the user's arms, device 500 provides additional capabilities for securing the article 502 to objects within the travel environment.

Figure 7B:
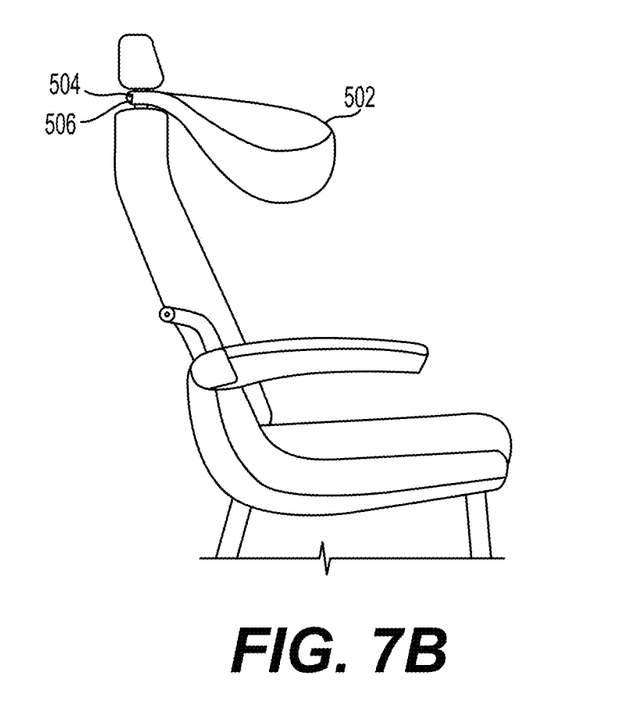
FIG. 7B shows an example use of the alternate embodiment shown in FIG. 7A, namely that the article is secured to a chair headrest for maintaining the upper body position of a user.
Figure 7C:
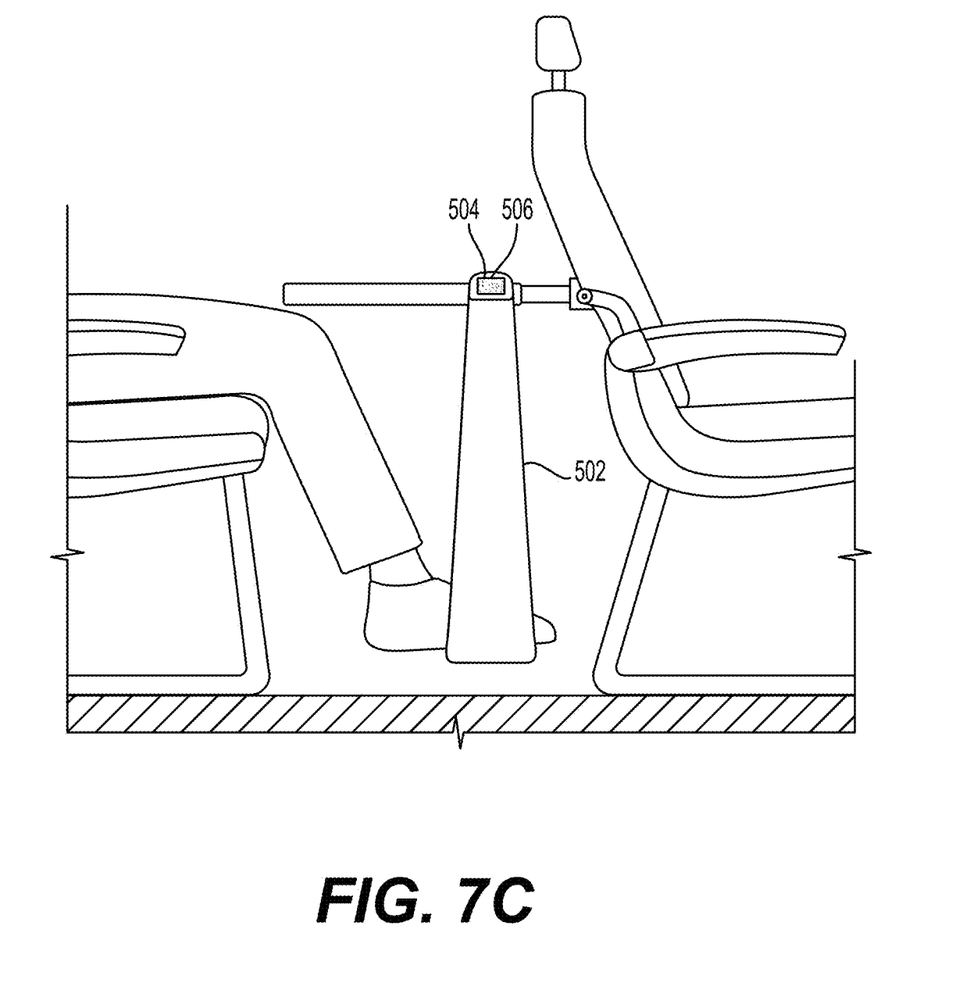
FIG. 7C shows an example use of the alternate embodiment shown in FIG. 7A, namely that the article is secured to a tray table for creating a suspended footrest.

As an example, the device 500 can be secured around the back of a chair headrest, as shown in FIG. 7B, with the article 502 extending forward for securing the user's arms. In this example, both the user's arm positions and upper body posture are maintained by the flexible article 502, such that the user can sleep or relax without falling forward or leaning too far in their seat. In another example use, the device 500 can be secured around a seat tray table and used to elevate one or both of the user's feet off the ground, as seen in FIG. 7C. This configuration provides the benefit of reducing pressure on the user's leg joints and improving circulation by elevating the feet off of the ground.

The example configurations shown in FIGS. 7B and 7C can be beneficial not only for comfort during travel, but also as a means of resistance exercise by pulling and pushing against the flexible article 502. In a further example, the flexible article 502 may be secured around a user's knees (not shown) in order to both maintain a preferred knee alignment, and to provide a means for exercising the legs and hips with resistive training. Further configurations and means of securing a user's preferred body postures and/or utilizing the device 500 for exercise maneuvers may be readily implemented by the product user without diverging from the scope of the claimed invention.

In further alternative embodiments, the resistive-band exercises using device 500 may instead be performed with any of the previous embodiments of the device 100, 200, 300, and 400. These previous embodiments may be modified such that they comprise a reinforcing elastic band or an article formed from a highly elastic material, either of which can be used in exercise or for additional functionalities during travel. The specific features, techniques, and capabilities of each described embodiment of the invention in no way is limited to the specific example embodiment with which it was disclosed, and any one example embodiment may interchangeably implement the features shown in other example embodiments.

Although specific embodiments and examples have been illustrated and described herein, any further arrangements or modifications which achieve the same purpose, structure, or function may be substituted for the specific embodiments shown. This application is intended to cover any additional adaptations or variations of the example embodiments of the invention described herein. These and other embodiments are within the scope of the following claims and their equivalents.

The invention claimed is:

1. A device for comfortably securing a user's arms while traveling, the device comprising:
    one or more sheets of a fabric material which are formed into an article with a rounded pouch shape, comprising a top side, a bottom side, a left elbow pocket, and a right elbow pocket; and
    a hollow opening, located on the top side of the article, for inserting the user's arms into the article;
    wherein the hollow opening is sized to accommodate one or more dimensions of the user's arms while in a comfortable folded posture; and
    wherein, the article is configured to provide a primary configuration and an alternative configuration, wherein in the primary configuration, the article wraps and supports user's arm independent of other body parts while providing a resistant compression force, preventing separation of the user's arms and maintaining the comfortable folded posture
    wherein in the alternative configuration, the article wraps around the user's arms and a fixed element within a travel environment, such that a preferred upper-body posture of the user can be supported by the device.

2. The device of claim 1, wherein the hollow opening is sized according to a fixed set of dimensions selected according to a plurality of pre-set user sizes.

3. The device of claim 1, further comprising an adjusting element configured to increase or reduce one or more dimensions of the hollow opening.

4. The adjusting element of claim 3, wherein the adjusting element comprises a fixing point located on an inner surface of the article which is fastened to an adjustable upper edge located on an inner fold loop of the article.

5. The adjusting element of claim 4, wherein the fixing point and the adjustable upper edge are connected via a hook and loop fastener.

6. The device of claim 3, wherein the left elbow pocket and the right elbow pocket are separated fabric elements, and wherein the left and right elbow pockets are connected to one another, at one or more of their ends, by one or more of the following:

an elastic band; or an adjustable strap.

7. The device of claim 1, wherein the article further comprises: an elastic band reinforcing and providing compression force on a top edge of the article's hollow opening.

8. The device of claim 1, wherein an outer surface of the article further comprises one or more decorative elements or printed images.

9. The device of claim 1, wherein the article further comprises an interior lining material which is comfortable for extended contact with human skin.

10. A system for comfortably securing a user's body during extended travel, the system comprising:

at least one device for securing a user's body position, the device comprising:

one or more sheets of a highly flexible fabric material, where one or more ends of the one or more sheets are secured together with a securing element to form an article with a rounded pouch shape, the article comprising a top side, a bottom side, a left elbow pocket, and a right elbow pocket; and a hollow opening, located on the top side of the article, for inserting the user's arms into the article;

wherein the hollow opening is sized to accommodate one or more dimensions of the user's arms while in a comfortable folded posture;

wherein, in a primary configuration, the device is sized to surround only the user's arms while providing a resistant compression force, preventing separation of the user's arms and maintaining the comfortable folded posture; and wherein, in one or more alternate configurations, the device performs one or more alternate functions, comprising:

wrapping the device around the user's arms and a fixed element within a travel environment, such that a preferred upper-body posture of the user can be supported by the device;

wrapping the device around the user's knees, providing a compression force which prevents the user's knees from spreading beyond a set distance; or wrapping the device around an object within the travel environment and the user's feet, to provide a suspended footrest.

11. The system of claim 10, wherein the one or more alternate functions further comprise configurations for performing exercise maneuvers, using the at least one device as a resistive elastic exercise band.

12. The system of claim 10, wherein the hollow opening of the at least one device is sized according to a fixed set of dimensions selected according to a plurality of pre-set user sizes.

13. The system of claim 10, wherein the securing element further comprises an adjusting element configured to increase or reduce one or more dimensions of the hollow opening.

14. The adjusting element of claim 13, wherein the adjusting element comprises a fixing point located on an inner surface of the article which is fastened to an adjustable upper edge located on an inner fold loop of the article.

15. The adjusting element of claim 14, wherein the fixing point and the adjustable upper edge are connected via a hook and loop fastener.

16. The system of claim 10, wherein the left elbow pocket and the right elbow pocket of the at least one device are separated fabric elements, and wherein the left and right elbow pockets are connected to one another, at one or more of their ends, by one or more of the following:

an elastic band; or an adjustable strap.

17. The system of claim 10, wherein the at least one device further comprises an elastic band reinforcing and providing compression force on a top edge of the article's hollow opening.

18. The system of claim 10, wherein an outer surface of the article of the at least one device further comprises one or more decorative elements or printed images.

19. The system of claim 10, wherein the at least one device further comprises a lining material on the interior of the article which is comfortable for extended contact with human skin.

20. A system for comfortably securing a user's body during travel on an airplane, the system comprising:

a plurality of devices, wherein each of the devices comprise:

one or more sheets of a highly flexible fabric material, where one or more ends of the one or more sheets are secured together with a securing element to form an article with a rounded pouch shape, the article comprising a top side, a bottom side, a left elbow pocket, and a right elbow pocket; and a hollow opening, located on the top side of the article, for inserting the user's arms into the article;

wherein the hollow opening is sized to accommodate one or more dimensions of the user's arms while in a comfortable folded posture;

wherein, in a primary configuration, the device is sized to surround only the user's arms to provide a resistant compression force which functionally replaces a traditional armrest, such that the user's arms are prevented from separating and remain in the comfortable folded posture;

wherein, in one or more alternate configurations, the device performs one or more alternate functions, comprising:

wrapping the device around the user's arms and a fixed element within a travel environment, such that a preferred upper-body posture of the user can be supported by the device;

wrapping the device around the user's knees, providing a compression force which prevents the user's knees from spreading beyond a set distance; or wrapping the device around an object within the travel environment and the user's feet, to provide a suspended footrest; and wherein the plurality of devices are implemented by the user in the primary configuration or the one or more alternate configurations.

\* \* \* \* \*